United States Patent
Ha et al.

(10) Patent No.: US 9,259,717 B2
(45) Date of Patent: Feb. 16, 2016

(54) CATALYST ACTIVATION METHOD FOR FISCHER-TROPSCH SYNTHESIS

(71) Applicant: KOREA RESEARCH INSTITUTE OF CHEMICAL TECHNOLOGY, Daejeon (KR)

(72) Inventors: Kyoung Su Ha, Daejeon (KR); Geun Jae Kwak, Daejeon (KR); Jae Hoon Jung, Daejeon (KR); Joo Young Cheon, Gwacheon-si (KR); Min Hee Woo, Gumi-si (KR); Yun Jo Lee, Daejeon (KR); Ki Won Jun, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 14/383,478

(22) PCT Filed: Mar. 7, 2013

(86) PCT No.: PCT/KR2013/001866
§ 371 (c)(1),
(2) Date: Sep. 5, 2014

(87) PCT Pub. No.: WO2013/133651
PCT Pub. Date: Sep. 12, 2013

(65) Prior Publication Data
US 2015/0018438 A1     Jan. 15, 2015

(30) Foreign Application Priority Data

Mar. 7, 2012  (KR) .................. 10-2012-0023668
Mar. 7, 2012  (KR) .................. 10-2012-0023669

(51) Int. Cl.
| | |
|---|---|
| *C07C 1/04* | (2006.01) |
| *B01J 23/96* | (2006.01) |
| *B01J 38/10* | (2006.01) |
| *B01J 38/04* | (2006.01) |
| *B01J 23/94* | (2006.01) |
| *B01J 23/89* | (2006.01) |
| *C22B 11/02* | (2006.01) |
| *C22B 23/02* | (2006.01) |
| *C22B 61/00* | (2006.01) |
| *C10G 2/00* | (2006.01) |
| *B01J 23/889* | (2006.01) |

(52) U.S. Cl.
CPC .............. *B01J 23/96* (2013.01); *B01J 23/8913* (2013.01); *B01J 23/94* (2013.01); *B01J 38/04* (2013.01); *B01J 38/10* (2013.01); *C07C 1/045* (2013.01); *C07C 1/0435* (2013.01); *C10G 2/333* (2013.01); *C10G 2/334* (2013.01); *C22B 11/02* (2013.01); *C22B 23/02* (2013.01); *C22B 61/00* (2013.01); *B01J 23/8896* (2013.01); *C07C 2529/068* (2013.01); *C10G 2300/4037* (2013.01)

(58) Field of Classification Search
CPC .............. C07C 1/04; C10G 2/00; C10G 2/32; C10G 2/33
See application file for complete search history.

(56) References Cited

U.S. PATENT DOCUMENTS

| | | | |
|---|---|---|---|
| 4,006,177 A | 2/1977 | Kiovsky et al. | |
| 6,509,382 B1 * | 1/2003 | Ducreux et al. | ............. 518/709 |
| 2004/0259963 A1 | 12/2004 | Huang et al. | |
| 2005/0124706 A1 * | 6/2005 | Wright et al. | ................. 518/726 |
| 2010/0081562 A1 | 4/2010 | Rotgerink | |

FOREIGN PATENT DOCUMENTS

WO     03/002252 A1    1/2003

OTHER PUBLICATIONS

Hammache et al., "Passivation of a Co—Ru/γ—$Al_2O_3$ Fischer-Tropsch catalyst," *Catalysis Today* 71:361-367 (2002).
Huber et al., "Remarks on the passivation of reduced Cu-, Ni-, Fe-, Co-based catalysts," *Catalysis Letters* 110(3-4):211-220 (2006).

* cited by examiner

*Primary Examiner* — Sudhakar Katakam
(74) *Attorney, Agent, or Firm* — Seed IP Law Group PLLC

(57) ABSTRACT

The present invention relates to: a catalyst activation method for Fischer-Tropsch synthesis; a catalyst regeneration method for Fischer-Tropsch synthesis; and a method for producing a liquid or solid hydrocarbon by using the Fischer-Tropsch synthesis reaction. The temperatures required for a metal carbide producing and activating reaction is markedly lower than existing catalyst activation temperatures, and the catalyst can be activated under conditions that are the same as Fischer-Tropsch synthesis reaction conditions, and thus there is no need for separate reduction equipment in the reactor, and a Fischer-Tropsch synthesis catalyst which has been used for a long time can be regenerated within the reactor without the catalyst being isolated or extracted from the reactor.

13 Claims, No Drawings

CATALYST ACTIVATION METHOD FOR FISCHER-TROPSCH SYNTHESIS

TECHNICAL FIELD

The present disclosure relates to a method for activating a catalyst for Fischer-Tropsch synthesis; a method for regenerating a catalyst for Fischer-Tropsch synthesis; and a method for producing liquid or solid hydrocarbon using a Fischer-Tropsch synthesis reaction.

BACKGROUND ART

In 1923, Fischer and Tropsch, German chemists, developed a Fischer-Tropsch synthesis method (F-T synthesis method), and this method has enabled the production of liquid hydrocarbon from coal, natural gas, biomass and the like by way of syngas. A process producing liquid hydrocarbon from coal is referred to as a coal-to-liquid (CTL) process, a process producing from natural gas is referred to as a gas-to-liquid (GTL) process, and a process producing from biomass is referred to as a biomass-to-liquid (BTL) process, and recently, similar processes are collectively referred to as XTL ("X" resource-to-liquid) processes.

These processes first convert each resource material (coal, natural gas, biomass and the like) into syngas using methods such as gasification and reforming, and the composition of the syngas suited for XTL processes for producing liquid fuel preferably has a hydrogen to carbon monoxide ratio of approximately 2 as shown in the following Reaction Formula 1.

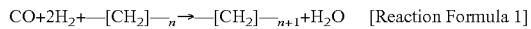

$$CO + 2H_2 + -[CH_2]-_n \rightarrow -[CH_2]-_{n+1} + H_2O \quad \text{[Reaction Formula 1]}$$

The ratio of hydrogen exceeding 2 is not preferable since it increases the selectivity on methane, and consequently, the selectivity on $C_{5+}$ (hydrocarbon having 5 or more carbon atoms) relatively decreases. In Reaction Formula 1, olefins and oxygenates (molecules including oxygen atoms such as alcohols, aldehydes, carboxylic acids and ketones) are also produced as byproducts in addition to hydrocarbon having linear chains as shown above.

One of the main purposes of XTL processes is to obtain liquid fuels, and therefore, the latest trend is to decrease selectivity on methane and to produce linear hydrocarbon, in particular, $C_{5+}$ linear hydrocarbon with high selectivity by optimizing a selection of reaction catalyst, a syngas ratio, a temperature, a pressure and the like. Herein, cobalt-series catalysts are normally used as the reaction catalyst, and such metal catalysts are used by being uniformly dispersed and supported on the surface of a support such as alumina, silica and titania. For the improvement of catalyst performances, noble metals such as Ru, Pt and Re may be used as a co-catalyst.

Such catalysts are normally used by being supported by a support such as alumina (—$Al_2O_3$, a-$Al_2O_3$ and the like), silica ($SiO_2$), titania ($TiO_2$) and magnesia (MgO). However, the use of silica materials having mesoporous structures such as SBA-15 and MCM-41, and carbon-based materials having mesoporous structures such as CMK-3 and carbon nanotubes has also been expanded recently. An incipient wetness method, an impregnation method and the like are normally used for such supports. For example, a target mass ratio of the catalyst material is supported in the pores of the support while repeatedly performing processes of dissolving a cobalt salt of acid ($Co(NO_3)_2 \cdot H_2O$ and the like), i.e., a catalyst precursor, and a salt such as Pt, Ru and Re used as a co-catalyst in proper solvents to prepare a mixed solution of the precursor, and impregnating the mixed solution of the precursor in the pores of the support, followed by drying. After that, the dried catalyst goes through a calcination process under air or inert gas atmosphere, and catalyst particles having a form in which cobalt oxide crystals are supported in the support are obtained.

A Fischer-Tropsch catalyst shows activity in a reduced metal state, and therefore, a syngas needs to be supplied in a pure metal state after sufficient reduction processes before reaction.

In a laboratory-scale experiment for developing catalysts, an in situ reduction method, in which the temperature is raised up to a reduction temperature while flowing a reducing gas with a calcinated catalyst to be filled into a reactor, is normally used. However, commercial reactors often employ other methods since reduction temperatures are generally much higher than reaction temperatures, and separate reducing gas injection equipment is required for an in situ reduction method.

In commercial processes, reduction is carried out by supplying reducing gas (a mixture of hydrogen and an inert gas where the hydrogen content is approximately 5 to 10%) with an additional catalyst reduction equipment. Cobalt metals in a reduced state violently react with oxygen in air and are oxidized again. Therefore, a proper treatment is necessary to not expose cobalt metals to air, or to minimize the degree of oxidation when exposed. Such a treatment is referred to as passivation, and by an intentional mild oxidation of the surface only through the supply of a mixed gas (normally consisting of oxygen and an inert gas) with a low concentration of oxygen, the activity of a catalyst can be minimally degraded when exposed to air during its transfer.

However, the passivation method has several problems. First, the degree of proper passivation is very difficult to identify. The degree of oxidation treatment required for minimizing violent oxidation during the air exposure is different for each catalyst. In addition, there are problems that initial activity is not satisfactory since oxidation has been partially progressed before use, and activity is generally low compared to an in situ reduction method.

In order to solve such problems, S. Hammache et al. (S. Hammache, J. G. Goodwin, Jr., R. Oukaci, Catalysis Today, 2002, 71, 361-367) designed a passivation method using CO gas or ($CO + H_2$) gas. However, the method has a problem in that the activity of a catalyst is degraded due to the production of graphitic carbon on the surface of the catalyst, and additionally, the method further requires a heating equipment capable of being operated at high temperatures in a reactor since the reduction process includes treating the catalyst with hydrogen gas for 10 hours at a high temperature of 350° C. when activating a carbide compound catalyst.

In addition, F. Huber et al. (F. Huber, H. Venvik, Catalysis Letters, 2006, 3-4, 211-220) proposed an encapsulation method using organic materials, a carbon layer coating method, a method of passivating metal catalysts through oxygen and $N_2O$ treatments. However, for activating, the method also requires reduction conditions of heating for 16 hours at a high temperature of 350° C. while supplying hydrogen gas.

Furthermore, various passivation methods carried out through the production of carbide and carbon have also been proposed in prior documents. WO 03/002252 discloses a method for transferring or activating a catalyst by passivating the activated catalyst using a method of coating the surface of a metal precursor material supported in a support with carbon by adding a certain amount (5 to 20%) of short-chained hydrocarbon (methane, ethane, etc.) together with hydrogen gas, or introducing a syngas, in order to produce a carbide form of a metal catalyst in a hydrogen reduction process.

Metal catalysts having a carbide form are known to have increased activity after activation, and the activity is known to be further improved when a metal carbide form is formed in certain parts of an activated metal catalyst. However, WO 03/002252 discloses that hydrogen reduction treatment at a high temperature of 350° C. or greater is necessary to activate the catalyst passivated in a metal carbide form, thus requiring an additional activation equipment in addition to the reaction equipment.

Meanwhile, even when an ex situ reduction method is used, a method without passivation by oxygen, that is, a method of introducing a catalyst directly into a reactor without being exposed to oxygen at all may be considered. However, the method also has problems. The catalyst reduction equipment and the reactor need to be relatively close, and the equipment may become larger since gas supply equipment, power, a heater and the like required for reduction all need to be included in a reactor system. In addition, there is a new challenging task on how to transfer solid particles from a catalyst reduction equipment to a reactor.

In order to solve these problems, Sasol Limited and Shell Oil Company and the like have devised methods in which, by coating a reduced catalyst with wax or inserting the reduced catalyst inside a wax material, the transfer of the catalyst becomes simple while capable of blocking its contact with air. However, because wax materials are solid at room temperature they need to be liquidified by heating in order to coat or insert catalyst particles, thus making the process complicated.

Meanwhile, an activated metal catalyst produces water and hydrocarbon compounds having various chain lengths by being reacted with a syngas. Performances of metal catalysts in a Fischer-Tropsch synthesis reaction are determined by the distribution of metal catalyst active sites and the degree of activation (degree of reduction), the interaction between catalysts and supports, the content of impurities in a syngas, and the degree of inactivation due to reaction products (wax and water) in the reaction, and performances of Fischer-Tropsch catalysts are determined by catalyst preparation methods, the choice of support/metal material and the presence of co-catalysts.

In the transformation of carbon monoxide, the performance of a cobalt catalyst is one of the most important factors in evaluating the economic feasibility of XTL processes. Particularly, hydrogenation reaction conversion ratio (CO conversion ratio) of carbon monoxide, which is a carbon source supplied by a syngas, and selectivity ($C_{5+}$ selectivity) of a linear hydrocarbon product having 5 or more carbon chains capable of being used as liquid fuels are important factors in evaluating catalyst performances. However, in addition to these, the degree of catalyst deactivation due to long-time operations greatly affects the choice of industrial catalysts in real processes. The main reasons for the deactivation of a cobalt metal catalysts in low temperature Fischer-Tropsch reactions carried out at 200 to 250° C. and 15 to 25 bar include the degradation of catalyst active sites due to catalyst poison such as sulfur and nitrogen compounds included in a syngas, the oxidation of cobalt metals, the formation of compounds between cobalt metals and supports, the degradation of active sites due to the sintering of small cobalt metal crystals, the recrystallization of atomic structures in cobalt metal surface, and the carbon deposition on active sites of cobalt, etc. Among these reasons, the main reasons for catalyst deactivation in real commercial plants include, along with the oxidation of the catalyst, the degradation of catalyst active sites due to long-chained wax products, and the blockage of catalyst pores, the degradation of active sites due to carbon deposition, the degradation of active sites due to the sintering of cobalt particles, and friction due to the collision of catalysts.

In real processes, the causes of catalyst deactivation such as sintering of cobalt particles, carbon deposition, and catalyst friction may be suppressed by changing reaction conditions of Fischer-Tropsch synthesis. For example, the sintering of cobalt particles occurs due to a sudden temperature increase in a catalyst unit in a circumstance where heat is not controlled, and cobalt particles supported in a support at a low Fischer-Tropsch reaction temperature condition of 210 to 230° C. almost do not experience sintering, therefore, catalyst deactivation due to sintering may be prevented when the heat generated from an exothermic reaction is effectively removed. Additionally, the degradation of catalyst activation due to carbon deposition may be diminished when a syngas with a $H_2/CO$ ratio of 2 is used as a reactant at proper reaction temperatures and pressures, since catalyst deactivation due to carbon deposition occurs when the ratio of carbon monoxide is high in the syngas, or the reaction is carried out at high temperatures and high pressures. In addition, activity degradation due to catalyst attrition may be diminished when a fixed-bed reactor or a slurry bubble column reactor having no catalyst damages due to impellers is used.

However, the degradation of active sites due to the wax produced by a reaction, and the degradation of catalyst activation due to the blockage of catalyst pores occur due to products. Therefore, the catalyst activity is gradually degraded reversibly according to the duration of reactions unless the reaction is stopped.

Accordingly, in the catalyst of which activity is degraded due to a long-time Fischer-Tropsch synthesis reaction, wax remaining on the catalyst surface blocks the active sites of the catalyst and is impregnated inside the pores. Therefore, reactivation is required to remove the wax and regenerate the active sites.

As existing reactivation methods of removing wax on a catalyst surface, US Patent Application Publication No. 2004/0259963 discloses a method for regenerating a catalyst including separating a catalyst present on slurry from the slurry for reactivation, de-waxing for removing wax, oxidizing the catalyst to an oxide form from a cobalt metal state, and reducing the catalyst again, thereby reactivating catalyst. In addition, US Patent Application Publication No. 2010/0081562 discloses a method for reactivating a catalyst including injecting a wax-coated catalyst into a pumpable liquid suspension, reactivating the catalyst by putting into contact with a high-temperature gas flow of 600 to 1050° C. for approximately 0.01 to 10 seconds, and separating the reactivated catalyst from the gas flow. US Patent Application Publication No. 2005/0124706 discloses a method including heat-treating a cobalt catalyst deactivated due to a long-term use several times for 4 hours at 300° C. under the atmosphere formed with 7 volume % of hydrogen and 93 volume % of vapor, and reactivating the catalyst to have 95% activity with respect to the initial catalyst activity through a carbon monoxide hydrogenation reaction.

However, the existing catalyst reactivation methods are inconvenient in that a catalyst needs to be reinjected after going through a process of extracting the catalyst inside a reactor out of the reactor and washing the catalyst when a fixed-bed reactor is used. When the reactivation is carried out inside a reactor to avoid such inconvenience, the temperature conditions of a reactivation reaction carried out by oxide formation and hydrogen are higher than Fischer-Tropsch synthesis reaction conditions, and consequently, the sintering of a cobalt metal catalyst may be induced. In addition, there are disadvantages in that the reactivation process including extraction and washing, oxidation, and reduction is rather complicated, and additional equipment needs to be installed around the reaction equipment.

Meanwhile, when a catalyst is regenerated in a fluidized-bed reactor, external equipment for separating the catalyst and fluidized liquid needs to be installed. Even when reactivation is carried out inside a reactor, the loss of fluidized liquid may occur when a reactivation temperature is above the boiling point of the fluidized liquid (350° C. or higher). In addition, there is a disadvantage in that, for the catalyst regeneration, costs for equipment for catalyst separation, regenerated gas supply, and heating additionally occur.

Existing catalyst regeneration methods have been developed with steps of catalyst separation, catalyst washing, catalyst oxidation, and catalyst reduction. Methods for simultaneously carrying out oxidation and reduction for simplifying the regeneration method, or for regenerating a catalyst inside a reactor without catalyst separation and washing have been proposed. However, only the number of steps in the process for catalyst regeneration decreases, and all the proposed methods commonly require a high-temperature heating of 300° C. or higher for final catalyst regeneration.

DISCLOSURE

Technical Problem

An objective of the present invention is to provide a method for activating a catalyst for a Fischer-Tropsch synthesis reaction at a low temperature similar to a Fischer-Tropsch synthesis reaction temperature.

Another objective of the present invention is to provide a method for activating a metal catalyst, which is capable of maintaining the catalyst activity for a long period of time and is convenient for long distance transfer.

Technical Solution

A first aspect of the present invention provides a method for activating a catalyst for Fischer-Tropsch synthesis comprising a first step of applying to a Fischer-Tropsch synthesis reactor, the metal carbide-containing catalyst for Fischer-Tropsch synthesis in which a part or all of the reduced metals, obtained by reducing a part or all of metal oxides in a metal oxide-containing catalyst for Fischer-Tropsch synthesis to metals, is converted to metal carbides by treating with a carbon monoxide-containing gas; and a second step of treating the metal carbide-containing catalyst for Fischer-Tropsch synthesis with hydrogen-containing gas in the reactor at a Fischer-Tropsch synthesis reaction temperature, thereby transforming the metal carbides to metals.

A second aspect of the present invention provides a method for preparing liquid or solid hydrocarbon using a Fischer-Tropsch synthesis reaction. The method includes a first step of applying to a Fischer-Tropsch synthesis reactor, the metal carbide-containing catalyst for Fischer-Tropsch synthesis in which a part or all of the reduced metals, obtained by reducing a part or all of metal oxides in a metal oxide-containing catalyst for Fischer-Tropsch synthesis to metals, is converted to metal carbides by treating with a carbon monoxide-containing gas; a second step of treating the metal carbide-containing catalyst for Fischer-Tropsch synthesis with hydrogen-containing gas in the reactor at a Fischer-Tropsch synthesis reaction temperature, thereby transforming the metal carbides to metals and activating the catalyst for Fischer-Tropsch synthesis; and a third step of carrying out a Fischer-Tropsch synthesis reaction using the activated catalyst.

A third aspect of the present invention provides a method for regenerating a catalyst for Fischer-Tropsch synthesis comprising a step a for forming metal carbides by treating the catalyst for Fischer-Tropsch synthesis, in which the activity therein is degraded due to the use in a Fischer-Tropsch synthesis reaction, with a carbon monoxide-containing gas; and a step b for treating the catalyst for Fischer-Tropsch synthesis, which is the result of the step a, with a hydrogen-containing gas, thereby transforming the metal carbides to metals.

A fourth aspect of the present invention provides a method for preparing liquid or solid hydrocarbon using a Fischer-Tropsch synthesis reaction. The method includes a step a for forming metal carbides by treating a catalyst for Fischer-Tropsch synthesis, in which the activity therein is degraded due to the use in the Fischer-Tropsch synthesis reaction, with carbon monoxide-containing gas; a step b for treating the catalyst for Fischer-Tropsch synthesis, which is the result of the step a, with a hydrogen-containing gas, thereby transforming the metal carbides to metals and regenerating the catalyst for Fischer-Tropsch synthesis; and a step c for carrying out a Fischer-Tropsch synthesis reaction using the regenerated catalyst.

In the methods according to the present invention, the metal is preferably cobalt, the metal oxide is preferably cobalt oxide, and the metal carbide is preferably cobalt carbide.

Hereinafter, the present invention will be described in detail.

The catalyst for Fischer-Tropsch synthesis in the present invention may include dried catalysts, calcinated catalysts, reduced catalysts and catalysts of which activity is degraded by being used in a Fischer-Tropsch synthesis reaction as described below.

The "dried catalyst" may include a catalyst in a dried state after supporting catalyst and/or co-catalyst precursors in a support using catalyst preparation methods such as an incipient wetness impregnation method, an impregnation method, a coprecipitation method, a sol-gel method, a chemical deposition method, a plasma method or a deposition-precipitation method, before calcination. Then, the dried catalyst goes through a calcination process for producing metal oxide crystals inside the pores of the support, and the calcination may be progressed in air or an inert gas atmosphere (for examples, gases that are not reactive such as nitrogen, helium and argon), and a catalyst after calcination refers to the "calcinated catalyst". The metal oxide crystals of the calcinated catalyst are reduced to metals using a reducing gas such as hydrogen in order to be used in Fischer-Tropsch synthesis, and the state is designated as the "reduced catalyst".

Meanwhile, catalysts used in syngas-using hydrocarbon synthesis reactions show catalyst deactivation by 5 to 10% after long-time reactions (at least 200 hours). The reasons for the deactivation of the used catalysts are mainly due to the influences of active site degradation due to wax, a product produced during the reaction, partial oxidation of a metal catalyst due to the water produced, and blockage of pores due to carbon deposition rather than the influences of catalyst breakage or catalyst poison.

$Co_3O_4 + 4CO \rightarrow 3Co + 4CO_2$ (first cobalt oxide reduction reaction)

$CoO + CO \rightarrow Co + CO_2$ (second cobalt oxide reduction reaction)

$2Co + 2CO \rightarrow Co_2C + CO_2$ (cobalt carbide production reaction)     [Reaction Formula 2]

$Co_2C + H_2 \rightarrow 2Co + —CH_2—$ (cobalt carbide activation reaction)     [Reaction Formula 3]

As shown in Reaction Formula 2, based on apparent stoichiometry, 4 moles of carbon monoxide reacts with 1 mole of first cobalt oxide ($Co_3O_4$) to reduce the first cobalt oxide to metal cobalt. 1 mole of carbon monoxide reacts with 1 mole of second cobalt oxide (CoO) to reduce the second cobalt oxide to metal cobalt. In the case of the metal cobalt, 2 moles of carbon monoxide reacts with 2 moles of chemical adsorption sites to produce 1 mole of cobalt carbide.

In addition, as shown in Reaction Formula 3, based on apparent stoichiometry, 1 mole of hydrogen is reacted with 1 mole of cobalt carbide to reduce the cobalt carbide to 2 moles of metal cobalt.

Accordingly, deactivated catalysts, which are obtained by activated cobalt catalysts being oxidized or carbidized through long-time operations or by the active site being degraded due to active site blockage, may be regenerated through a step of forming cobalt carbide by treating with carbon monoxide-containing gas [Reaction Formula 2]; and a step of hydrogenating the cobalt carbide to cobalt metal by treating the cobalt carbide with a hydrogen-containing gas [Reaction Formula 3].

Herein, the present invention provides a method for activating a catalyst for Fischer-Tropsch synthesis according to the first aspect of the present invention, and a method for regenerating a catalyst for Fischer-Tropsch synthesis according to the third aspect of the present invention based on the idea that the reactions described in Reaction Formula 2 and/or the reaction described in Reaction Formula 3 may be carried out in a Fischer-Tropsch synthesis reactor at a Fischer-Tropsch synthesis reaction temperature. In other words, the present invention reduces a catalyst for Fischer-Tropsch synthesis at low temperatures such as a Fischer-Tropsch synthesis reaction temperature in a Fischer-Tropsch synthesis reactor when activating/regenerating the catalyst by applying the fact that a catalyst for Fischer-Tropsch synthesis may be reduced to cobalt metal at a Fischer-Tropsch synthesis reaction temperature when being converted to $Co_2C$.

In the present invention, the catalyst for Fischer-Tropsch synthesis may be supported by a support such as silica, alumina, titania, zeolite, a mesopore carbon structure, a carbon nanotube, mesopore silica, a silica/alumina mixture, a titania/silica mixture and an alumina/titania mixture. The metal-containing catalyst for Fischer-Tropsch synthesis may further include co-catalyst metals such as platinum (Pt), palladium (Pd), rhodium (Rh), ruthenium (Ru) and rhenium (Re).

In the first and second aspects of the present invention, the first step is a step for treating a catalyst for Fischer-Tropsch synthesis in which a part or all of metal oxides in a metal oxide-containing catalyst for Fischer-Tropsch synthesis are reduced to metals with a carbon monoxide-containing gas in order to convert a part or all of the reduced metals in the catalyst for Fischer-Tropsch synthesis to metal carbides, and applying the metal carbide-containing catalyst to a Fischer-Tropsch synthesis reactor.

Herein, the catalyst for Fischer-Tropsch synthesis in which a part or all of the metal oxides in the metal oxide-containing catalyst for Fischer-Tropsch synthesis are reduced to metals may be obtained by:

(1) reduction treating the metal oxides with hydrogen at high temperatures;

(2) partly reducing the metal oxides to metals by treating the calcinated catalyst obtained after calcination with a gas mixture including carbon monoxide in 5 to 100% under an atmosphere of 5 bar or greater, and at a temperature of 300° C. to 450° C.; or (3) partly reducing the metal oxides to metals by treating the dried catalyst, which is obtained after supporting the catalyst precursor using methods such as impregnation and then drying, with a gas mixture including carbon monoxide in 5 to 100% at a temperature of 300° C. to 450° C.

In the cases of (2) and (3), some may be carbidized immediately after being reduced to metals.

Herein, the gas mixture may further include one or more types of inert gas selected from the group consisting of nitrogen, hydrogen, helium, neon, argon, krypton, zenon and radon, and types thereof are not limited as long as the gas does not react with the catalyst.

In the case of (2), reduction treatment by hydrogen at high temperatures may not be included. In addition, produced water is not generated in the activation step in (2), therefore, the activated catalyst does not experience re-oxidation at high temperatures and high pressures (or pressurization). Producing nano-scale catalyst crystals without water production, which is a byproduct, is one of the most important factors in catalyst preparation methods. This is due to the fact that nano-catalyst crystals in smaller than certain sizes are readily oxidized under oxidation atmosphere, and are very difficult to be reduced again Particularly, when using a crystalline support having mesopores, such as SBA-15, MCM-41 and CMK-3, produced water is locked inside the pores thereby facilitating re-oxidation, and consequently, interactions between the metal catalyst catalysts and the support increase, resulting in the production of metal-support oxide complexes that are irreducible.

In the case of (3), a calcination process, which is a step of producing oxide crystals, and a pre-reduction process by a hydrogen-containing gas mixture, which is an activation step prior to the reaction, is not included.

In the first step, the process of treating carbon monoxide-containing gas to the catalyst for Fischer-Tropsch synthesis in which a part or all of metal oxides are reduced to metals uses a gas mixture including carbon monoxide in 5 to 100%, and 50% or greater of the reduced metals may be converted to metal carbides at a Fischer-Tropsch synthesis reaction temperature. When using a cobalt catalyst, the Fischer-Tropsch synthesis reaction temperature is normally in the range of from 200° C. to 300° C.

Herein, the carbon monoxide-containing gas may further include one or more types of inert gases selected from the group consisting of nitrogen, hydrogen, helium, neon, argon, krypton, zenon and radon, and types thereof are not limited as long as the gas does not react with the catalyst. Being treated with carbon monoxide, the inert gas may function as a carrier gas facilitating the travel of carbon monoxide and also function to adjust the concentration.

The carbide compound produced as above is exposed to air for at least 1 hour, and may induce the oxygen being removed more readily by a syngas, which is reducing gas during the reaction, through reacting with carbon materials present in the catalyst.

The metal carbide catalyst is hardly oxidized even when being exposed to air, therefore, may be stored in air for a long period of time. In addition to this, an oxidizer such as water is not generated during the process of carbide production, and therefore, the carbide may be prepared in a stable form. However, carbon monoxide experiences molecular decomposition when carbidization is carried out at extremely high temperatures, thus causing carbon deposition. Catalysts with carbon deposition do not exhibit the propoer activities of a catalyst since carbon adsorbs to the pores and the catalyst active sites, therefore, precautions are required. In addition to this, when carbon consistently accumulates in the pores, the catalyst may be broken or split due to wedge phenomena leading to the generation of fine particles, and this causes an increase in the pressure difference between the top and the bottom of a reactor in a fixed-bed reactor, and causes the clog of a filter installed to filter the catalyst and products in a fluidized-bed reactor. The process up to this part is called a passivation process, and there are no problems in activating the catalyst at this state even when the catalyst has been exposed for a quite long period of time.

The second step in the first aspect and the second aspect of the present invention is a step of activating the catalyst for Fischer-Tropsch synthesis by treating the metal carbide-containing catalyst for Fischer-Tropsch synthesis with hydrogen-containing gas in the reactor at a Fischer-Tropsch synthesis reaction temperature, thereby transforming the metal carbides to metals.

The present invention carries out the transformation reaction to metals under mild conditions such as a Fischer-Tropsch synthesis reaction temperature when the catalyst is activated in a Fischer-Tropsch synthesis reactor including the catalyst.

When a cobalt catalyst is used, the Fischer-Tropsch synthesis reaction temperature normally ranges from 200° C. to 300° C.

Herein, the hydrogen-containing gas preferably contains hydrogen in 5% to 100%, and may further include one or more types of an inert gas selected from the group consisting of nitrogen, helium, neon, argon, krypton, zenon and radon. The inert gas may function as a carrier gas facilitating the travel of hydrogen and also function to adjust the concentration.

Meanwhile, the step a in the third aspect and the fourth aspect of the present invention is a step for forming metal carbides by treating the catalyst for Fischer-Tropsch synthesis, in which the activity therein is degraded due to a Fischer-Tropsch synthesis reaction, with a carbon monoxide-containing gas.

The catalyst for Fischer-Tropsch synthesis of which activity is degraded has a form that a part or all of the catalyst in a metal state are reduced to metal oxides.

The carbon monoxide-containing gas step a is referred to as a reaction gas distinguished from a syngas, and is preferably formed with 10% to 100% of carbon monoxide, with the remainder being a carrier gas mixture. The carrier gas may usually include nitrogen and helium. Other descriptions on the carbon monoxide-containing gas are the same as those defined in the first step.

Carbon monoxide actually reacts with the catalyst used, and the oxidized catalyst is reduced by the carbon monoxide, and the metal state forms a carbon compound, that is, carbide.

The carbide may be produced at a reaction temperature ranging from 200° C. to 250° C., and a reaction pressure ranging from atmospheric pressure to 25 bar. Therefore, when a catalyst needs to be regenerated during a Fischer-Tropsch synthesis reaction, carbide may be produced just by changing gas supply from syngas to carbon monoxide gas in the same reaction condition.

Accordingly, the step a is preferably carried out at a temperature ranging from 200° C. to 250° C. When carbidization is carried out at extremely high temperatures, carbon monoxide experiences molecular decomposition. As a result, carbon deposition occurs, and catalysts with carbon deposition do not properly exhibit activities as a catalyst since carbon adsorbs to the pores and the catalyst active sites. In addition, the step a may be carried out at a pressure ranging from 1 bar to 25 bar.

The gas stream required for carbidization may be used in a very wide flow rate range through the reactor used in a hydrocarbon synthesis reaction. An optimal flow rate varies depending on the variables such as a reaction temperature, a pressure, particle sizes, the types of a support or channel sizes. The flow rate may be measured by the volume of a reaction gas (including a carrier gas and a reaction gas) per mass per time of the injected catalyst, which is called as a gas hourly space velocity (GHSV), the GHSV for the catalyst carbidization may be in the range from 100 to 10,000 $hr^{-1}$, preferably at least from 500 $hr^{-1}$ to 1,500 $hr^{-1}$ or less, and more preferably from 800 to 1,000 $hr^{-1}$. When the flow rate of the reaction gas is outside the range described above, the carbidization efficiency may decrease.

The duration of the carbidization reaction is determined by stoichiometry, for example, the amount of the cobalt metal supported, the concentration of the reaction gas and the flow rate of the reaction gas. The carbidization reaction is quick, and the completion of the reaction may be measured by monitoring the exhaust gas with respect to the reaction gas using gas chromatography. 3 to 5 hours are required for carbidization in preferable temperature and pressure ranges.

Meanwhile, the step b in the third aspect and the fourth aspect of the present invention is a step of reactivating, that is, regenerating the catalyst for Fischer-Tropsch synthesis by transforming metal carbides to metals by treating the catalyst for Fischer-Tropsch synthesis, which is the result of the step a, with hydrogen-containing gas.

Through the present invention, it is identified that the catalyst may be regenerated under conditions similar to the conditions required for carbide formation (low temperature activation) using a reducing gas, which is different from existing catalyst regeneration methods in which a catalyst is activated through reduction at high temperatures. The carbidized catalyst provided in the present invention seems to induce low reducing temperatures, which is different from existing reduction reactions after oxidation described above.

The descriptions on the hydrogen-containing gas are the same as those on the hydrogen-containing gas defined in the second step of the first aspect and the second aspect.

In the step b, the hydrogen-containing gas is referred to as a hydrogenating gas, and preferably contains hydrogen gas in the amount of from 10% to 100%, and the rest may be a carrier gas mixture. The carrier gas may usually include nitrogen and helium. Hydrogen reacts with the carbidized catalyst, and the carbidized catalyst is converted to a metal catalyst by the reaction with hydrogen. Based on apparent stoichiometry, 1 mole of hydrogen reacts with 1 mole of cobalt carbide to be reduced to 2 moles of metal cobalt (refer to Reaction Formula 3).

The activation of carbidized catalyst may be carried out at a reaction temperature ranging from 200° C. to 300° C. and a reaction pressure ranging from atmospheric pressure to 25 bar, therefore, when regeneration is required during the carbidization reaction, the catalyst may be reactivated just by changing gas supply to transforming gas in the same carbidization reaction condition.

The step b may be carried out at a pressure ranging from 1 bar to 25 bar.

The gas stream in the step b may be used in a very wide flow rate range through the chamber in which the carbidization is progressed. An optimal flow rate varies depending on the variables such as a reaction temperature, a pressure, particle sizes, the types of a support or channel sizes. The gas hourly space velocity (GHSV) in the step b may be in the range from 100 to 10,000 $hr^{-1}$, preferably at least from 500 $hr^{-1}$ to 1,500 $hr^{-1}$ or less, and more preferably from 800 to 1,000 $hr^{-1}$.

The duration of the reaction is determined by stoichiometry, that is, the amount of the cobalt metal supported, the concentration of the reaction gas, and the flow rate of the reaction gas. The step b is quick, and the completion of the reaction may be measured by monitoring the exhaust gas with respect to the reducing gas using gas chromatography. Particularly, the completion of the reactivation reaction may be determined according to the amount of the short-chain hydrocarbon produced in the reaction. 3 to 5 hours are required for the step b in preferable temperature and pressure ranges.

When the carbidized catalyst is reactivated using a transforming gas, the cobalt metal crystal structure is mostly converted to a hexagonal close-packed lattice (hcp) from a face-centered cubic structure (fcc), and in a Fischer-Tropsch synthesis reaction, the hcp structure is more advantageous than the fcc structure in terms of activities. Accordingly, the catalyst regeneration method provided in the third aspect and the fourth aspect of the present invention has an effect of activity increase through the structural change of the cobalt metal in addition to the active site recovery effect due to an wax removal effect at suitable temperatures in the step a and step b, and also.

The step a and step b may be carried out inside a reactor in which the Fischer-Tropsch synthesis reaction occurs. In the present invention, the reactor may be a slurry reactor, a fixed bed reactor, a multi-channel reactor or a continuous stirring tank reactor.

In addition, at least one of the step a and step b may be carried out outside a reactor in which the Fischer-Tropsch synthesis reaction occurs.

For example, the step a may be carried out inside a reactor in which the Fischer-Tropsch synthesis reaction occurs, and the step b may be carried out outside a reactor in which the Fischer-Tropsch synthesis reaction occurs. Herein, a step of collecting and storing the cobalt catalyst produced in the step a may be further included after the step a. The metal carbide compound formed in the step a is hardly oxidized even when being exposed to air. Therefore, it may be stored in air for a long period of time, and the carbide may be prepared in a stable form since an oxidizer such as water is not generated during the process of carbide production. Accordingly, the catalyst may be regenerated through the reactivation reaction of the step b, however, the used catalyst may be readily reactivated by being stored after carbidization, or being injected to another reactor for catalyst analysis and catalyst activity tests.

In addition, by further including the step of collecting the catalyst of which activity is degraded due to the use in the Fischer-Tropsch synthesis reaction from a reactor in which the Fischer-Tropsch synthesis reaction occurs before the step a, the step a and step b may be carried out outside a reactor in which the Fischer-Tropsch synthesis reaction is carried out.

Furthermore, the step a may be carried out outside a reactor in which the Fischer-Tropsch synthesis reaction occurs, and the step b may be carried out inside a reactor in which the Fischer-Tropsch synthesis reaction occurs. Herein, a step of collecting the catalyst of which activity is degraded due to the use in the Fischer-Tropsch synthesis reaction from a reactor in which the Fischer-Tropsch synthesis reaction may be further included before the step a, and step a of introducing the metal carbide into a reactor in which the Fischer-Tropsch synthesis reaction occurs may be further included before the step b.

Meanwhile, the third step in the second aspect and the step c in the fourth aspect of the present invention is step a for carrying out the Fischer-Tropsch synthesis reaction using the activated/regenerated catalyst. It may be carried out at a reaction temperature of 200° C. to 350° C. (preferably 200° C. to 240° C.), a reaction pressure of 5 to 30 kg/cm$^3$ (preferably 1.0 to 2.5 MPa), and a space velocity of 1,000 to 12,000 h$^{-1}$ (preferably 2,000 to 10,000 h$^{-1}$), however, the reaction conditions are not limited thereto. In addition, the Fischer-Tropsch synthesis reaction is preferably carried out while maintaining the hydrogen/carbon monoxide reaction ratio at a molar ratio of 1 to 2.

In addition, the method for preparing hydrocarbon according to the present invention may further include a reforming reaction step of Fischer-Tropsch synthesis reaction products after the third step and/or the step c.

Advantageous Effects

By using a catalyst reduction method according to a first aspect and a second aspect of the present invention, the degradation of catalyst activities due to passivation may be prevented, and inconvenient processes such as wax insertion may not be included as well. In addition, the catalyst may be activated under the same conditions as Fischer-Tropsch synthesis reaction conditions, therefore, separate reduction facilities are not required in a reactor. Furthermore, the catalyst may be prepared in advance outside a reactor and immediately used when necessary. Catalyst activity may be maintained even after long-time transfer/storage since passivation-treated catalysts are not oxidized in air.

Moreover, by using a catalyst regeneration method provided in the third aspect and the fourth aspect of the present invention, catalysts may be reactivated without separating or extracting the catalyst for Fischer-Tropsch synthesis used for a long period of time, and in this method, the temperatures required for metal carbide production and reactivation reactions needed in the catalyst regeneration process are markedly lower than existing catalyst regeneration temperatures. Therefore, the method of the present invention has favorable industrial applicability since separate heating facilities and regeneration facilities are not required.

MODE FOR DISCLOSURE

Hereinafter, the present invention will be described in details with reference to the following examples. However, these examples are for illustrative purposes only, and the scope of the present invention is not limited to these examples.

Preparation Example 1 to Preparation Example 3

Dried Catalyst, Calcinated Catalyst and Reduced Catalyst

A dried catalyst was prepared by drying a catalyst having a composition of 0.05Pt-24Co/1.5Si/alumina (numbers in front of the elements represent mass ratios of the corresponding elements included in the catalyst) for 12 hours at 110° C. using an impregnation method (Preparation Example 1), a calcinated catalyst was prepared by calcinating some of the dried catalyst for 5 hours at 400° C. (Preparation Example 2), and a reduced catalyst was prepared by treating 150 g of the calcinated catalyst under atmospheric pressure for 12 hours at 400° C. using 2 SLPM of a hydrogen-containing gas (10% H$_2$/He) (Preparation Example 3).

EXAMPLE 1

Catalyst Activation Using Reduced Catalyst

The reduced catalyst prepared in Preparation Example 3 was carbidized for 5 hours at 220° C. and 2.0 MPa using 2 SLPM of 100% CO gas, and was placed into contact with air for at least 1 hour by taking out the reduced catalyst in air. Next, 0.5 g of the catalyst was transferred to a reactor for Fischer-Tropsch synthesis and then filled, and after that, a reduction process was carried out for 5 hours at 220° C., and 9 bar using 100 SCCM of 5% $H_2$/He.

EXAMPLE 2

Catalyst Activation Using Calcinated Catalyst

The calcinated catalyst prepared in Preparation Example 2 was reduced through CO for 12 hours at a space velocity of 5000 ml CO/g-cat/h, a reaction temperature of 350° C. and a reaction pressure of 20 bar, and catalyst carbidization was induced for 5 hours by lowering the temperature to 220° C. at the same space velocity. A reduction process was carried out in the same manner as in Example 1 by purging the catalyst for 10 minutes using nitrogen, taking out and exposing the catalyst in air for at least 1 hour, and then transferring the catalyst to a reactor.

EXAMPLE 3

Catalyst Activation Using Dried Catalyst

The dried catalyst prepared in Preparation Example 1 was reduced through CO for 12 hours at a space velocity of 5000 ml CO/g-cat/h, a reaction temperature of 350° C. and a reaction pressure of 20 bar, and catalyst carbidization was induced for 5 hours by lowering the temperature to 220° C. at the same space velocity. A reduction process was carried out in the same manner as in Example 1 by purging the catalyst for 10 minutes using nitrogen, taking out and exposing the catalyst in air for at least 1 hour, and then transferring the catalyst to a reactor.

EXAMPLE 4

Catalyst Activation Carrying Out Carbidization Under Atmospheric Pressure

The reduced catalyst prepared in Preparation Example 3 was carbidized for 5 hours at 220° C. and under atmospheric pressure using 2 SLPM of 100% CO gas. A reduction process was carried out in the same manner as in Example 1 by purging the catalyst for 10 minutes using nitrogen, taking out and exposing the catalyst in air for at least 1 hour, and then transferring the catalyst to a reactor.

EXAMPLE 5

Catalyst Activation Carrying Carbidization Under Reduced Pressure

The reduced catalyst prepared in Preparation Example 3 was carbidized for 5 hours at 220° C. and under reduced pressure of 0.1 Torr using 2 SLPM of 100% CO gas. A reduction process was carried out in the same manner as in Example 1 by purging the catalyst for 10 minutes using nitrogen, taking out and exposing the catalyst in air for at least 1 hour, and then transferring the catalyst to a reactor.

Comparative Example 1

Intrinsic Fischer-Tropsch Catalyst Activation that does not go Through Passivation Process After drying a catalyst having a composition of 0.05Pt-24Co/1.5Si/alumina for 12 hours at 110° C. using an impregnation method, and then calcinating for 5 hours at 400° C., activation was carried out by reduction treating 0.3 g of the catalyst for 5 hours at 400° C. under atmospheric pressure using 80 SCCM of hydrogen-containing gas (5% $H_2$/He) with a reactor being filled with the catalyst.

Comparative Example 2

Squalene-Coated Catalyst Activation

The reduced catalyst prepared in Preparation Example 3 was carbidized for 5 hours at 220° C. and 2.0 MPa using 2 SLPM of 100% CO gas, and then inserted for at least 1 hour by inserting the catalyst into squalene bubbled with nitrogen for 24 hours. 0.3 g of the catalyst was transferred to a synthesis reactor with the squalene being coated thereon, and then the reactor was filled with the catalyst. After that, a reduction process was carried out for 5 hours at 220° C. and 9 bar using 100 SCCM of 5% $H_2$/He.

Comparative Example 3

Catalyst Activation Through Passivation Using Oxygen

The reduced catalyst prepared in Preparation Example 3 was passivated by flowing an $O_2$/He mixture gas containing oxygen in 2% for 2 hours at room temperature. After that, the catalyst was transferred to a reactor, and a reduction process was carried out in the same manner as in Example 1.

Test Example

Fischer-Tropsch Synthesis Reaction

Conversion ratios and selectivity were identified by carrying out a Fischer-Tropsch synthesis reaction using the activated catalysts prepared in the examples and the comparative examples. The reactor used in the tests was a micro reactor, wherein the pipe has a diameter of 9.525 mm, a height of the catalyst-filled layer of 20 to 35 mm, the ratio of the catalyst and a diluent was 1:5 (weight ratio), the size of the catalyst ranged from 50 to 150 μm, and the diluent having a similar size to the catalyst was used. A reaction temperature ranged from 220 to 230° C., a reaction pressure was 2.0 MPa, and a space velocity was 4,000 SCCM of syngas/g-cat/h, and a syngas composition of $H_2$/CO/$CO_2$/Ar=57.3/28.4/9.3/5 was used.

1) Result of Fischer-Tropsch Synthesis Reaction of Activated Catalyst in Comparative Example 1

TABLE 1

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 72.2 | 3.1 | 3.8 | 93.1 |
| 230 | 4000 | 93.0 | 3.8 | 3.9 | 92.3 |

Comparative Example 1 is an in situ reduction, and both reactivity and selectivity are favorable, however, this method is normally suitable for laboratory scale experiments. A high temperature reduction operation (400° C. or higher) needs to be directly carried out in a field reactor. Therefore, a specially manufactured reactor needs to be used so that an additional reduction equipment or reduction conditions are accommodated. Water is generated during the reduction, therefore, additional facilities (steam tracing, a condenser and the like) are required in order to readily remove the water.

2) Result of Fischer-Tropsch Synthesis Reaction of Activated Catalyst in Example 1

TABLE 2

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 66.9 | 3.1 | 3.2 | 93.6 |
| 230 | 4000 | 89.4 | 3.6 | 3.1 | 93.3 |

Example 1 is a mild reduction carried out in the field after carrying out passivation in a facility producing a catalyst and then transferring the catalyst to the field. Both reactivity and selectivity were sufficiently high comparable to the activity of the in situ reduction method (Comparative Example 1). In addition, the possibility of successful passivation and activation was identified by exposing the catalyst to air for a certain period of time after carbidizing the catalyst. The catalyst activated through Example 1 had low risks since the step of the in situ reduction directly carried out with a hydrogen-containing gas in a high-temperature reactor may not be included in the process. In the mild reduction, water was not generated as a byproduct, and all removed in the form of $CO_2$.

3) Result of Fischer-Tropsch Synthesis Reaction of Activated Catalyst in Comparative Example 2

TABLE 3

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 51.0 | 3.5 | 3.8 | 92.7 |
| 230 | 4000 | 74.3 | 4.2 | 3.9 | 92.0 |

As shown in Table 3, it was identified that the performance of the catalyst that is not exposed to air after carbidization was inferior compared to that of the catalyst exposed to air as in Example 1.

4) Result of Fischer-Tropsch Synthesis Reaction of Activated Catalyst in Comparative Example 3

TABLE 4

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 30.2 | 10.6 | 8.8 | 80.6 |
| 230 | 4000 | 44.8 | 11.5 | 8.9 | 79.6 |

Comparative Example 3 shows a mild reduction after passivating the reduced catalyst with low-concentrated $O_2$, and as shown in Table 4, it was identified that the conversion ratio and the selectivity were low compared to the catalysts activated through Examples 1 and 2.

5) Result of Fischer-Tropsch Synthesis Reaction of Activated Catalyst in Example 2

TABLE 5

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 41.0 | 8.2 | 6.3 | 85.4 |
| 230 | 4000 | 64.9 | 8.1 | 5.9 | 86.0 |

Example 2 excludes a hydrogen reduction step carried out at a high temperature, and directly carbide passivates the calcinated catalyst. As shown in Table 5, the activity of the activated catalyst using the calcinated catalyst was rather inferior due to the differences in the degree of reduction. However, it was identified that the conversion efficiency and the selectivity were more superior compared to Comparative Example 3, although the conversion efficiency was rather low compared to that of Comparative Example 2 where air exposure was prevented.

6) Result of Fischer-Tropsch Synthesis Reaction of Activated Catalyst in Example 3

TABLE 6

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 36.4 | 8.0 | 8.2 | 83.8 |
| 230 | 4000 | 59.2 | 10.2 | 10.4 | 79.4 |

As shown in Table 6, it was identified that the catalyst activated using the dried catalyst had a rather low conversion efficiency compared to that of the catalyst in Comparative Example 2 where air exposure was prevented. However, compared to that of the catalyst in Comparative Example 3, the conversion efficiency and the selectivity were similar or more superior.

7) Result of Fischer-Tropsch Synthesis Reaction of Activated Catalyst in Example 4

TABLE 7

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 81.61 | 5.81 | 5.54 | 88.65 |

As shown in Table 7, the catalyst experiencing atmospheric pressure carbidization had more superior conversion efficiency and selectivity compared to those of the catalyst in Comparative Example 2 where air exposure was prevented, and those of the catalyst in Comparative Example 3 where the catalyst was passivated by oxygen.

8) Result of Fischer-Tropsch Synthesis Reaction of Activated Catalyst in Example 5

TABLE 8

| T (° C.) | SV (ml/g-cat/h) | Conversion Total Conv (CO) | Hydrocarbon selectivity | | |
|---|---|---|---|---|---|
| | | | $C_1$ | $C_2$-$C_4$ | $C_{5+}$ |
| 220 | 4000 | 75.95 | 6.49 | 6.15 | 87.37 |

As shown in Table 8, the catalyst experiencing reduced pressure carbidization had more superior conversion efficiency and selectivity compared to those of the catalyst in Comparative Example 2 where air exposure was prevented, and those of the catalyst in Comparative Example 3 where the catalyst was passivated by oxygen.

Preparation Example 4

Preparation of Catalyst

As a catalyst, a catalyst having a composition of 0.05Pt/24Co/1.5Si/alumina (numbers in front of the elements represent mass ratios of the corresponding elements included in the catalyst) was dried for 12 hours at 110° C. using an impregnation method and then calcinated for 5 hours at 400° C. After that, a suitable amount of the catalyst for each reactor was injected to the reactor. The catalyst was activated for 12 hours at 400° C. under atmospheric pressure using a space velocity corresponding to the amount of the catalyst injected with a gas containing 5 volume % of hydrogen, and then used in a Fischer-Tropsch synthesis reaction.

EXAMPLE 6

As a multi-channel reactor, a reactor having a structure of 5 catalyst layers and 4 heat exchange layers between the catalyst layers was used. The heat exchange layer was formed with micro-structured channels and vapor was used as a heat exchange medium. The weight of the catalyst was 45 g, the height of the filled catalyst was 90 mm, the ratio of the catalyst and the diluent was 1:1.5 in a weight ratio, the size of the catalyst ranged from 50 to 150 μm (the size of the diluent was similar to that of the catalyst), and the catalyst was filled to an identical height into the 5 catalyst layers. Inside the reactor, a K-type temperature system was placed into contact with the catalyst layer, and the reaction temperature was controlled using internal heat media and external heat sources. The reaction temperature was employed to range from 220 to 240° C., the reaction pressure to be 2.0 MPa (20 bar), and the space velocity to be 4000 $h^{-1}$. Herein, the Fischer-Tropsch synthesis reaction was carried out for at least 300 hours with the composition of the syngas being $H_2$/CO/$CO_2$/Ar=57.3/28.4/9.3/5 (volume %). After the initial activity of the cobalt metal catalyst activated with 5 volume % of hydrogen was normalized to 1, the Fischer-Tropsch synthesis reaction was carried out for 300 hours, and the catalyst activity decreased to 0.91 with respect to the initial activity of the metal catalyst. Herein, the syngas was converted to a pure carbon monoxide gas (reaction gas) in order to regenerate the catalyst. The reaction conditions were maintained to be the same as the Fischer-Tropsch synthesis conditions. Herein, the catalyst was carbidized by injecting 0.7 L of carbon monoxide per minute for 5 hours. The carbon monoxide gas (reaction gas) was converted to a pure hydrogen gas (transforming gas) in order to reactivate the carbidized catalyst. The reaction conditions were maintained to be the same as the carbidization reaction conditions. Herein, the catalyst was reactivated by injecting 1 L of hydrogen gas per minute for 5 hours. After the catalyst was reactivated, the activity of the reactivated catalyst was compared with that of the initial catalyst.

TABLE 9

| Status | Activity[a] ($\mu mol_{CO}g_{Co}^{-1}s^{-1}$) | $C_{5+}$ Time Yield[b] ($10^{-4}s^{-1}$) | Relative Intrinsic FTS Activity Factor | Relative Intrinsic FTS $C_{5+}$ Time yield Factor | CO Conversion | $C_{5+}$ Selectivity |
|---|---|---|---|---|---|---|
| Initial Stage | 46.60 | 23.63 | 1.00 | 1.00 | 79.39 | 87.25 |
| After 300 Hours | 42.20 | 20.38 | 0.91 | 0.86 | 71.89 | 82.43 |
| Regenerated | 50.41 | 23.52 | 1.08 | 0.996 | 85.89 | 80.91 |

[note]
[a]Activity: number of moles of carbon monoxide reacting in 1 g of the cobalt metal for 1 second
[b]$C_{5+}$ time yield: number of moles of carbon monoxide reacting to $C_{5+}$ hydrocarbon in the Co catalyst supported in the catalyst for 1 second As shown in Table 9, it was identified that the activity of the regenerated catalyst increased by 8% or greater compared to the initial activity of the cobalt catalyst going through the steps of catalyst injection and activation. In addition, the amount of $C_{5+}$ production according to time ($C_{5+}$ time yield), which has important influences on a Fischer-Tropsch synthesis process, decreased by 14% or greater after at least 300 hours of operation. However, it was identified that the catalyst was regenerated to its original efficiency through the catalyst regeneration process going through the steps of carbidization and reactivation.

Comparative Example 4

After the Fischer-Tropsch synthesis reaction was carried out in the same manner as in Example 6, the catalyst was carbidized in the same manner as in Example 6, and the Fischer-Tropsch synthesis reaction was carried out without reactivation. The activity of the cobalt catalyst in the Fischer-Tropsch synthesis reaction was measured in the same manner as in Example 6.

TABLE 10

| Status | Activity[a] ($\mu mol_{CO}g_{Co}^{-1}s^{-1}$) | $C_{5+}$ Time Yield[b] ($10^{-4}s^{-1}$) | Relative Intrinsic FTS Activity Factor | Relative Intrinsic FTS $C_{5+}$ Time Yield Factor | CO Conversion | $C_{5+}$ Selectivity |
|---|---|---|---|---|---|---|
| Initial Stage | 46.60 | 23.63 | 1.00 | 1.00 | 79.39 | 87.25 |
| After 300 Hours | 50.41 | 23.52 | 1.08 | 0.996 | 85.89 | 80.91 |
| Carbidized | 2.23 | 0.82 | 0.05 | 0.035 | 3.81 | 73.08 |

[note]
[a]Activity: number of moles of carbon monoxide reacting in 1 g of the cobalt metal for 1 second
[b]$C_{5+}$ time yield: number of moles of carbon monoxide reacting to $C_{5+}$ hydrocarbon in the Co catalyst supported in the catalyst for 1 second As shown in Table 10, the carbide-treated catalyst had a significantly low activity compared to that of the activated (initial) and the reactivated catalyst, and was non-reactive to the Fischer-Tropsch synthesis reaction. Accordingly, it was confirmed that the carbidized catalyst needs to be used after being regenerated by reactivation through the same as method described in Example 6.

EXAMPLE 7

After the catalyst used in the Fischer-Tropsch synthesis reaction was carbidized as in Example 6, the catalyst was separated and 5 g of the carbidized catalyst was inserted into a continuous stirring tank reactor (CSTR) together with 300 ml of squalene. The reactivation of the carbidized catalyst was carried out in the CTST prior to the Fischer-Tropsch synthesis reaction. The catalyst reactivation reaction was carried out for 5 hours at a reactivation temperature of 220° C. and a reaction pressure of 20 bar with hydrogen gas having a space velocity of 800 hr$^{-1}$. The activity of the reactivated catalyst was compared with the activity of the initial catalyst after reactivating the catalyst in the CSTR reactor. The reaction conditions for the comparison were as follows. The reaction temperature was 220° C., the reaction pressure was 2.0 MPa (20 bar), and the space velocity was 4,000 h$^{-1}$. Herein, the composition of the syngas was H$_2$/CO/CO$_2$/Ar=57.3/28.4/9.3/5 (volume %).

TABLE 11

| Status | Activity[a] ($\mu mol_{CO}g_{Co}^{-1}s^{-1}$) | $C_{5+}$ Time Yield[b] ($10^{-4}s^{-1}$) | Relative Intrinsic FTS Activity Factor | Relative Intrinsic FTS $C_{5+}$ Time Yield Factor | CO Conversion | $C_{5+}$ Selectivity |
|---|---|---|---|---|---|---|
| Initial Stage in CSTR | 34.06 | 17.92 | 1 | 1 | 58.03 | 89.26 |
| Regenerated in CSTR | 41.09 | 22.78 | 1.21 | 1.272 | 70.00 | 94.10 |

[note]
[a]Activity: number of moles of carbon monoxide reacting in 1 g of the cobalt metal for 1 second
[b]$C_{5+}$ time yield: number of moles of carbon monoxide reacting to $C_{5+}$ hydrocarbon in the Co catalyst supported in the catalyst for 1 second As shown in Table 11, it was identified that the used catalyst may be applied to other reactors by being carbidized and readily extracted from the reactor, and after the regeneration, catalyst properties more superior than the intrinsic catalyst activity and the $C_{5+}$ productivity were exhibited.

Comparative Example 5

After a catalyst having a composition of 0.05Pt/24Co/1.5Si/alumina (numbers in front of the elements represent mass ratios of the corresponding elements included in the catalyst) was dried for 12 hours at 110° C. using an impregnation method and calcinated for 5 hours at 400° C., 5 g of the cobalt catalyst in an oxidized state was inserted into a CSTR with 300 ml of squalene.

Generally, the activation of a cobalt catalyst in an oxidized state is carried out outside by bringing the oxidized cobalt catalyst back to a metal cobalt state with heating at a temperature of 400° C. under a reducing gas atmosphere, and the reaction is progressed by inserting the cobalt catalyst activated as described above into a CTSR with squalene without contacting air. However, in Comparative Example 5 of the present invention, a cobalt catalyst in an oxidized state was reduced for 5 hours inside a CSTR at a reaction temperature of 220° C. and a reaction pressure of 20 bar with hydrogen gas having a space velocity of 800 hr$^{-1}$, in order to compare the results of activating oxidized cobalt and carbidized cobalt using the same reduction method. After the reduction, a Fischer-Tropsch reaction was progressed, and the reaction conditions were as follows. The reaction temperature was 220° C., the reaction pressure was 2.0 MPa (20 bar), and the space velocity was 4,000 h$^{-1}$. Herein, the composition of the syngas was H$_2$/CO/CO$_2$/Ar=57.3/28.4/9.3/5 (volume %).

TABLE 12

| Status | Activity[a] ($\mu mol_{CO}g_{Co}^{-1}s^{-1}$) | $C_{5+}$ Time Yield[b] ($10^{-4}s^{-1}$) | Relative Intrinsic FTS Activity Factor | Relative Intrinsic FTS $C_{5+}$ Time Yield Factor | CO Conversion | $C_{5+}$ Selectivity |
|---|---|---|---|---|---|---|
| Initial Stage in CSTR | 34.06 | 17.92 | 1 | 1 | 58.03 | 89.26 |
| Regenerated in CSTR | 41.09 | 22.78 | 1.21 | 1.272 | 70.00 | 94.10 |
| Mild Reduction of Oxide Form | 3.30 | 1.88 | 0.10 | 0.105 | 5.63 | 96.62 |

[note]
[a]Activity: number of moles of carbon monoxide reacting in 1 g of the cobalt metal for 1 second
[b]$C_{5+}$ time yield: number of moles of carbon monoxide reacting to $C_{5+}$ hydrocarbon in the Co catalyst supported in the catalyst for 1 second Through Table 12, it was identified that, when the oxidized cobalt was activated in the reactor using the same reduction method as the carbidized cobalt, the catalytic activity was not recovered to the original level. Accordingly, it was confirmed that a reduction process needs to be carried out after going through carbidization in order to regenerate a cobalt catalyst.

The invention claimed is:

1. A method for preparing liquid or solid hydrocarbon using a Fischer-Tropsch synthesis reaction, comprising:
   (1) exposing a metal carbide-containing catalyst to air obtain a passivated catalyst, and applying to the passivated catalyst to a Fischer-Tropsch synthesis reactor, wherein the metal carbide-containing catalyst is obtained from a reaction in which a part or all of a reduced metal-containing catalyst is converted to metal carbide-containing catalyst by treating the reduced metal-containing catalyst with a carbon monoxide-containing gas, and wherein the reduced metal-containing catalyst is obtained by reducing the metal oxide in a metal oxide-containing catalyst;
   (2) treating the metal carbide-containing catalyst of step (1) with hydrogen-containing gas in the reactor at a Fischer-Tropsch synthesis reaction temperature ranging from 200° C. to 300° C., thereby transforming the metal carbides to a metals and obtaining an activated catalyst; and
   (3) carrying out a Fischer-Tropsch synthesis reaction using the activated catalyst of step (2).

2. The method of claim 1, wherein the metal is cobalt, the metal oxide is cobalt oxide, and the metal carbide is cobalt carbide.

3. The method of claim 1, wherein the metal carbide-containing catalyst of step (1) is obtained by treating the reduced metal-containing catalyst with the carbon monoxide-containing gas at a Fischer-Tropsch synthesis reaction temperature ranging from 200° C. to 300° C.

4. The method of claim 1, wherein the reduced metal-containing catalyst is a dried catalyst or a calcinated catalyst comprising metal oxides, and wherein a part or all of the metal oxides in the dried catalyst or calcinated catalyst is reduced using the carbon monoxide-containing gas at a temperature ranging from 300° C. to 450° C.

5. The method of claim 1, wherein the metal carbide-catalyst is supported in any one support selected from the group consisting of silica, alumina, titania, zeolite, a mesopore carbon structure, a carbon nanotube, mesopore silica, a silica/alumina mixture, a titania/silica mixture, and an alumina/titania mixture.

6. The method of claim 1, wherein the metal-containing catalyst for further includes one or more types of co-catalyst metals selected from the group consisting of platinum (Pt), palladium (Pd), rhodium (Rh), ruthenium (Ru) and rhenium (Re).

7. A method for preparing liquid or solid hydrocarbon using a Fischer-Tropsch synthesis reaction, comprising:
   a. forming metal carbides by treating a catalyst for Fischer-Tropsch synthesis, with a carbon monoxide-containing gas at a Fischer-Tropsch synthesis reaction temperature ranging from 200° C. to 300° C. to obtain a metal carbide-containing catalyst, wherein the activity of the catalyst has been degraded in a first Fischer-Tropsch synthesis reaction, and wherein the carbon monoxide-containing gas is not a syngas containing carbon monoxide and hydrogen;
   b. treating the metal carbide-containing catalyst of step a with a hydrogen-containing gas at a Fischer-Tropsch synthesis reaction temperature ranging from 200° C. to 300° C. in an Fischer-Tropsch synthesis reactor, thereby transforming the metal carbides to metals and obtaining a regenerated catalyst; and
   c. carrying out a second Fischer-Tropsch synthesis reaction using the regenerated catalyst.

8. The method of claim 7, wherein the metal carbide is cobalt carbide.

9. The method of claim 7, wherein step a or step b are each independently carried out inside a reactor in which the second Fischer-Tropsch synthesis reaction is carried out.

10. The method of claim 7, wherein step a or step b are each independently carried out outside a reactor in which the Fischer-Tropsch synthesis reaction is carried out.

11. The method of claim 7, further comprising collecting and storing the metal carbide-containing catalyst of step a.

12. The method of claim 7, wherein the catalyst for Fischer-Tropsch synthesis is supported by any one support selected from the group consisting of silica, alumina, titania, zeolite, a mesopore carbon structure, a carbon nanotube, mesopore silica, a silica/alumina mixture, a titania/silica mixture and an alumina/titania mixture.

13. The method of claim 8, wherein the catalyst for Fischer-Tropsch synthesis further includes one or more types of co-catalyst metals selected from the group consisting of platinum (Pt), palladium (Pd), rhodium (Rh), ruthenium (Ru) and rhenium (Re).

* * * * *

UNITED STATES PATENT AND TRADEMARK OFFICE
CERTIFICATE OF CORRECTION

PATENT NO.        : 9,259,717 B2
APPLICATION NO.   : 14/383478
DATED             : February 16, 2016
INVENTOR(S)       : Kyoung Su Ha et al.

It is certified that error appears in the above-identified patent and that said Letters Patent is hereby corrected as shown below:

Claims

Column 21, Lines 27-28, Claim 1:
"(1) exposing a metal carbide-containing catalyst to air obtain a passivated catalyst," should read,
--(1) exposing a metal carbide-containing catalyst to air to obtain a passivated catalyst,--.

Column 21, Lines 40-41 Claim 1:
"thereby transforming the metal carbides to a metals" should read, --thereby transforming the metal carbides to a metal--.

Column 21, Lines 55-56, Claim 4:
"metal oxides in the dried catalyst or calcinated catalyst is reduced" should read, --metal oxide in the dried catalyst or calcinated catalyst is reduced--.

Column 21, Lines 59-60, Claim 5:
"5. The method of claim 1, wherein metal carbide-catalyst is supported in any one support" should read, --5. The method of claim 1, wherein metal carbide-containing catalyst is supported in any one support--.

Column 22, Lines 18-19, Claim 6:
"6. The method of claim 1, wherein the metal-containing catalyst for further includes one or more types of co-catalyst" should read, --6. The method of claim 1, wherein the metal-containing catalyst further includes one or more types of co-catalyst--.

Signed and Sealed this
Second Day of August, 2016

Michelle K. Lee
*Director of the United States Patent and Trademark Office*